United States Patent [19]
Lin et al.

[11] Patent Number: 5,157,190
[45] Date of Patent: * Oct. 20, 1992

[54] PROCESS FOR PREPARING OLEFINS BY BUTENE DISPLACEMENT

[75] Inventors: Kaung-Far Lin; William H. Beaver; Neal J. Colonius; William B. Waites, all of Baton Rouge, La.

[73] Assignee: Ethyl Corporation, Richmond, Va.

[*] Notice: The portion of the term of this patent subsequent to Jun. 19, 2007 has been disclaimed.

[21] Appl. No.: 502,791

[22] Filed: Apr. 2, 1990

[51] Int. Cl.$^5$ ............................................. C07C 2/88
[52] U.S. Cl. .................................. 585/512; 585/511; 585/522
[58] Field of Search ........................ 585/511, 512, 522

[56] References Cited

U.S. PATENT DOCUMENTS

| | | | |
|---|---|---|---|
| 2,863,896 | 12/1958 | Johnson | 260/448 |
| 2,889,385 | 6/1959 | Catterall et al. | 260/683.15 |
| 3,286,992 | 11/1966 | Armeniades et al. | 259/4 |
| 3,721,719 | 3/1973 | Fernald et al. | 585/522 |
| 3,789,081 | 1/1974 | Lanier | 585/522 |
| 4,380,684 | 4/1983 | Fowler et al. | 585/328 |
| 4,935,569 | 6/1990 | Harkins et al. | 585/522 |

FOREIGN PATENT DOCUMENTS 717116 8/1965 Canada ............................. 585/522

Primary Examiner—Asok Pal
Attorney, Agent, or Firm—David M. Bunnell

[57] ABSTRACT

An improved process for making olefins from a lower olefin such as ethylene and an alkyl aluminum by chain growth employs a butene displacement reaction using mixing device such as a static mixer which permits efficient operation of the displacement reaction at moderate pressures where the reactants form a two-phase vapor-liquid system or a vapor system.

16 Claims, 1 Drawing Sheet

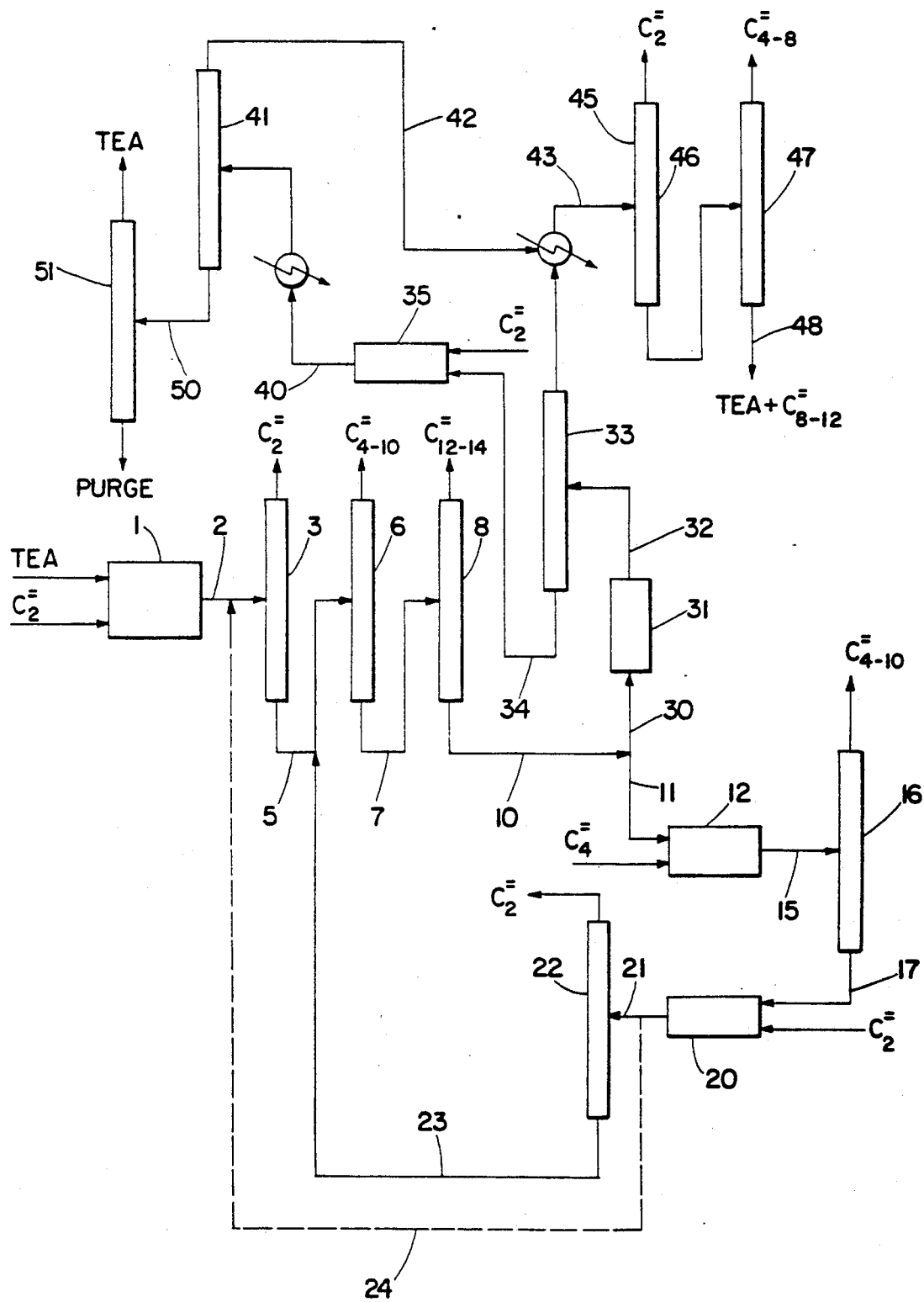

PROCESS FOR PREPARING OLEFINS BY BUTENE DISPLACEMENT

BACKGROUND

This invention relates generally to the preparation of higher olefins using a chain growth reaction of a lower olefin and especially ethylene with a low molecular weight alkyl aluminum and more specifically to such processes using an improved butene displacement reaction to displace the higher olefins from the aluminum, which permits efficient operation of the displacement reaction at pressures where the reaction mixture is in the two-phase, vapor-liquid or the vapor-phase regions.

Alpha-olefins are made in commercial quantities by a process initially developed in the fifties by Karl Ziegler and his co-workers. The so-called Ziegler process involves the reaction of triethyl aluminum ("TEA") and ethylene at temperatures in the range of 200°-500° F. and pressures in the ran 2000-5000 psig to yield a mixture of tri-$C_{2-20+}$ alkyl aluminum having a Poisson alkyl distribution and $C_{2-20}$ olefins. The ethylene is flashed from the reaction mixture for recycle and the light olefins through decene-1 can be distilled from the mixed aluminum alkyls since they have a normal boiling point below the lightest aluminum alkyl (viz. TEA).

Johnson, U.S. Pat. No. 2,863,896, describes the preparation of pure aluminum alkyls using a chain growth reaction of a $C_{2-4}$ olefin (e.g. ethylene) with a low molecular weight trialkyl aluminum (e.g. TEA), dialkyl aluminum hydride or alkyl aluminum dihydride. The chain growth product contained about 2-5 percent $C_{4-20}$ olefin which could not be separated from the aluminum alkyls. The mixture was then subjected to a displacement reaction with a $C_{4-6}$ $\alpha$-olefin, e.g. 1-butene, to displace mainly $C_{6-20}$ $\alpha$-olefin forming tributyl aluminum. The $C_{6-20}$ $\alpha$-olefins were fractionated into individual $\alpha$-olefins. These individual $\alpha$-olefin cuts were then reacted in a second displacement reaction with the tributyl aluminum formed in the butene displacement reaction to form pure trialkyl aluminum.

Catterall et al., U.S. Pat. No. 2,889,385, describes an ethylene chain growth reaction carried out on tributyl aluminum followed by displacement with 1-butene to regenerate tributyl aluminum and evolve $C_{4-20}$ $\alpha$-olefins. This avoids the problem encountered in attempting to separate TEA from $C_{12-14}$ $\alpha$-olefins which have normal boiling points close to the same temperature.

Other patents disclosing variations of the aluminum alkyl chain growth $\alpha$-olefin synthesis are U.S. Pat. Nos. 2,906,794; 2,971,969; 3,180,881; 3,210,435; 3,227,773; 3,278,633; 3,352,940; 3,663,647; 3,789,081; 3,487,097, 4,314,090; 3,359,292; 3,384,651; 3,415,861; 3,458,594 and 3,358,050.

All aluminum alkyl chain growth products initially yield a mixture of higher trialkyl aluminum compounds exhibiting a Poisson distribution. When ethylene and TEA are used, the mixture is mainly tri-$C_{2-20}$ alkyl aluminum compounds although a small amount of $C_{20+}$ alkyls are usually present. Ethylene displacement of this mixture yields a mixture of $C_{2-20}$ olefins. The more valuable components are the $C_{6-14}$ $\alpha$-olefins. Ethylene can be recycled to chain growth and olefins above $C_{14}$ can be separated for use as diluent or can be purged. Butene is produced in fairly large amounts and cannot economically be discarded. The commercial market for butene is substantially saturated. Copending application Ser. No. 373,247 provides a process that utilizes the butene that it produces in a closed butene displacement loop that gives high yield of the more desirable $C_{6-12}$ $\alpha$-olefins. The displacement reaction is carried out at pressures of about 1000 to 2000 psig. Operation at lower pressures where the reaction mixture passes from a single liquid phase to a two-phase vapor-liquid or a vapor-phase system has been found to result in breaking down of the aluminum alkyl with resulting formation of deposits on the reactor walls which may even plug a small diameter tubular reactor.

We have discovered that by providing enhanced radial mixing of the reactants, the displacement reaction can be smoothly carried out at a range of pressures from 2000 psig down to at least about 65 psig without deposits. This permits the use of relatively low pressure butene displacement.

SUMMARY

In accordance with this invention, there is provided an improved process for making higher $\alpha$-olefins from ethylene by chain growth comprising feeding ethylene and an alkyl aluminum compound to a reaction zone maintained under chain growth conditions to produce tri-$C_{2-20+}$ alkyl aluminum compounds and then feeding at least a part of said tri-$C_{2-20+}$ alkyl aluminum compounds and butene as reactants to a displacement zone maintained under displacement conditions to form a butene displaced product comprising mainly tri-butyl aluminum, ethylene and $C_{4-20+}$ $\alpha$-olefins, the improvement comprising employing in said displacement zone a flow through reactor and providing radial mixing of said butene and tri-$C_2$-$C_{20+}$ alkyl aluminum in said reactor.

DESCRIPTION OF THE DRAWING

The drawing is a schematic flow diagram of an alpha-olefin preparation process which incorporates the improved butene displacement step of the process of the invention. Conventional equipment such as valves, pumps, heaters, coolers and the like have not been included in the drawing for the sake of improved clarity.

In the drawing, olefins are designated as C= with a subscript showing the number of carbon atoms. Hence $C_2$= is ethylene and $C_4$= is butene. A Poisson distribution of trialkyl aluminum is designated by "p" followed by "tri-$C_n$ alkyl aluminum" where the subscript "n" represents the number of carbon atoms in the alkyl groups or a range of carbon atoms in the alkyl groups. For example "p tri-$C_{2-20}$ alkyl aluminum" represents a mixture of trialkyl aluminums in which the alkyl groups contain from 2 to 20 carbon atoms. The moles of each particular alkyl group in the mixture varies in a Poisson distribution. Those familiar with aluminum alkyl chain growth chemistry will recognize that small amounts of alkyls having more than 20 carbon atoms may be present. Also an olefin designated as C=$_{4-10}$ will generally contain a residual amount of C=$_2$ and also a small amount of olefin above decene because it is not economically practical to have distillation fractions any purer than this.

DETAILED DESCRIPTION

Although the process of the invention is useful with any chain growth process involving an alkyl displacement step for higher $\alpha$-olefin product recovery, a specific example of such a process is described in detail in copending application U.S. Ser. No. 373,247 and now U.S. Pat. No. 4,935,569 whose teachings are incorporated herein by reference. Referring to the drawing, such a process is schematically illustrated. The illustrated process includes ethylene chain growth, a 2-stage ethylene displacement loop and a butene displacement-ethylene displacement loop. In the drawing ethylene ("$C_2=$") and triethyl aluminum ("TEA") are fed to first ethylene chain growth reactor 1 in a mole ratio of about 4-10/1. Chain growth reactor 1 is maintained under chain growth conditions. These are a temperature in the range of about 200°-500° F., more preferably 225°-350° F., and a pressure of about 2000-5000 psig, more preferably 2000-3500 psig. Residence time of ethylene and TEA in chain growth reactor 1 should be long enough to increase the chain length of the alkyls bonded to aluminum to a mole average chain length of about 6-12 carbon atoms. Depending on temperature and pressure, a residence time on the order of 15 minutes to about 1 hour is usually satisfactory.

The first chain growth product formed in chain growth reactor 1 is conveyed via conduit 2 into vapor-liquid separator 3 which is at a lower pressure than chain growth reactor 1 causing most of the residual ethylene in the first chain growth product to vaporize and be removed overhead. All ethylene streams separated in the process are recycled to one of the ethylene chain growth reactors or ethylene displacement reactors which consume all the separated ethylene.

The ethylene-depleted first chain growth product from separator 3 is transferred via conduit 5 to distillation unit 6 which serves to distill out $C_{4-10}$ olefins. Distillation unit 6 is shown as a single unit but is preferably a series of 2-3 separation units each in sequence at a lower pressure than the preceding unit.

The bottoms from distillation unit 6 are transferred via conduit 7 to a mid-point in vacuum rectification column 8. Column 8 is operated in a range of about 5-30 torr (5-30 mm mercury or about 0.1 to 0.6 psia) with its reboiler adjusted to maintain reflux conditions in the rectification zone above the mid-point in a temperature range of about 200°-250° F. Under these conditions, 1-dodecene together with some 1-decene and 1-tetradecene are distilled overhead with little contamination by TEA which has about the same normal boiling point.

The $C_{4-14}$ olefins removed are transferred to a distillation area (not shown) where they are combined with olefins recovered from other sections of the overall process and fractionated to recover butene for feed to the butene displacement unit to be described later and to form olefin fractions, e.g. 1-octene, 1-decene, 1-dodecene, suitable for sales. In an optional embodiment other $C_{4-8}$ α-olefins can be combined and used as feed to the butene displacement reactor in which case it should be referred to as a $C_{4-8}$ olefin displacement reactor. Generally, the olefins in excess over demand in the overall process are butenes and especially 1-butene. Linear low density polyethylene (LLDPE) provide a market for all 1-hexene. Excess 1-octene can be combined with the butenes as feed to the $C_{4-8}$ olefin displacement reactor. However, in a most preferred embodiment the $C_{4-8}$ olefin is mainly, i.e. 60-100 weight percent and preferably 75-100 weight percent and most preferably 90-100 weight percent, butenes. 1-butene can be used alone as well as mixtures of butenes containing up to about 80 wt % 2-butene (20-100 wt % 1-butene).

The bottoms stream from vacuum column 8 comprises mainly Poisson distributed tri-$C_{2-20}+$ alkyl aluminums and $C_{14}+$ olefins. A portion of this stream depending on the amount of 1-butene available but generally about 75-95 weight percent is conveyed via conduits 10 and 11 to butene displacement zone 12.

In a preferred embodiment of the improved process of the invention, butene displacement zone 12 comprises a flow through tubular "T" reactor having a mixing tee, with inlet tubes for the aluminum alkyls and butene, and a thermocouple to monitor the feed temperature. The reactor is provided with means to accomplish thorough and rapid radial mixing of the reactants such that the material at the center of the reactant stream is repeatedly forced to the outer wall of the reactor and back again. A preferred device for accomplishing such mixing is a static mixer which includes a series of alternating right and left-handed helices. Such static mixing devices are commercially available (Chemineer Kenics Mixers) and are described in U.S. Pat. No. 3,286,992. The helices are alternated and oriented so that each leading edge is at 90° to the trailing edge of the one ahead. This device imparts both flow division and radial mixing with plug-flow of the reactants. Efficient butene displacement is achieved even at temperatures and pressures such that the reaction mass is a two-phase, vapor-liquid system or a vapor-phase system, without decomposition of the aluminum alkyls and/or deposit formation on the walls of the reactor. Other configurations of static mixing elements, which impart rapid and thorough mixing of the reactants and are effective to prevent excessive deterioration of the aluminum alkyls, can also be employed. Another example of a suitable static mixer is a Koch SMV static mixer (Koch Engineering Co., Inc.) which comprises a plurality of deflection plates forming a tortuous path through the mixer causing extremely turbulent flow. Such static mixing devices can constitute the entire reactor or just the front end of the reactor. Other suitable methods and arrangements to obtain thorough radial mixing of the reactants such as, for example, sonic mixing can also be used and the process of the invention is not limited to any particular manner of accomplishing such mixing. Depending upon the reaction conditions and composition of the reaction mass such radial mixing may be needed in only the first part of the reactor e.g., about the first 1/10 to ½ of the length of the reactor, in order to achieve a satisfactory result.

Zone 12 is maintained under displacement conditions. Temperatures of about 500°-750° F. are suitable. A range of pressures of 2000 psig down to about 50 psig can be used. Moderate pressures of 150 to 800 psig can be advantageously used to provide efficient exchange without decomposition and/or deposit formation. Heretofore, operation at pressures of about 150 psig, where the reactants are in a vapor or vapor-liquid phase, without providing radial mixing has been found to result in decomposition of the aluminum compounds and aluminum deposits on the reactor walls.

In operation, 1-butene, or a mixture of 1-butene and 2-butene, is pumped into zone 12 in an amount sufficient to provide about 2.5-50 moles of butene per mole of aluminum alkyl. The displacement reaction is fast. An average residence time of about 0.1 to 2 second is usually adequate. This results in butene displacement of most of the alkyl groups bonded to aluminum forming a butene-displaced product comprising mainly tributyl aluminum, residual tri-$C_{2-20}$ alkyl aluminum, ethylene and $C_{4-20}+$ α-olefins.

The butene-displaced product is transferred via conduit 15 to distillation unit 16 which functions to flash off ethylene and distill out $C_{4-10}$ α-olefins. The ethylene is recycled to chain growth and the $C_{4-10}$ olefins are transferred to the distillation area mentioned earlier for separation into various fractions.

The bottoms stream from distillation unit 16 is transferred via conduit 17 to second ethylene chain growth reactor 20 maintained under chain growth conditions. These conditions are the same as in the first ethylene chain growth reaction zone, i.e. 200°–500° F., 2000–5000 psig, residence time 15 minutes to 1 hour. Ethylene is fed to second ethylene chain growth reactor 20 in an amount sufficient to increase the average chain length of the alkyls to about 6–8 carbon atoms. This usually requires about 3–6 moles of etylene per mole of aluminum alkyl. This results in a second chain growth product comprising mainly ethylene, $C_{4-20}$ α-olefins and tri-$C_{4-20}$ alkyl aluminum.

The second chain growth product is conveyed via conduit 21 to ethylene separator 22 wherein ethylene is flashed off at a lower pressure. The ethylene-depleted liquid phase from separator 22 comprises mainly $C_{4-20}$ α-olefins and tri-$C_{2-20}$ alkyl aluminums and is conveyed via conduit 23 back to conduit 5 leading to distillation unit 6, thus completing the butene loop. In an alternate arrangement, second chain growth product from reactor 20 is transferred from conduit 21 via conduit 24 (shown as dashed line) to vapor-liquid separator 3 wherein ethylene separation is performed.

Preferably, only part of the bottoms stream from vacuum column 8 was conveyed to butene displacement zone 12. The remainder is subjected to an ethylene displacement loop. In this embodiment, the remaining portion of the bottoms stream from rectification column 8 is conveyed via conduit 30 to ethylene displacement zone 31 maintained under ethylene displacement conditions. These are about 450°–700° F. at 200–400 psig with an average residence time of 0.1–5 seconds. Ethylene is also pumped into displacement zone 31 in an amount sufficient to displace most of the non-ethyl alkyl groups bonded to aluminum. This requires about 5–10 moles of ethylene per mole of aluminum alkyl. This results in an ethylene displaced product comprising mainly TEA, ethylene and $C_{4-20}+$ α-olefins. In one embodiment, this stream is subject to a flash vaporization to remove most of the ethylene and the liquid phase is further distilled to remove $C_{4-12}$ α-olefins and the distillation bottoms are recycled to the first ethylene chain growth reaction zone.

In a second embodiment the ethylene displacement loop uses two ethylene displacement operations. In this embodiment, ethylene displacement zone 31 is referred to as first ethylene displacement zone 31. The amount of ethylene pumped to displacement zone 31 is adjusted such that under the displacement conditions used, only about 75–95 mole percent of the aluminum alkyls form TEA resulting in a partially displaced product comprising mainly ethylene, tri-$C_{2-20}$ alkyl aluminum and $C_{4-20}$ α-olefins.

The partially displaced product is conveyed via conduit 32 to distillation unit 33 which functions to distill out $C_{2-12}$ olefins and part of the TEA forming a bottoms fluid comprising mainly tri-$C_{2-20}$ alkyl aluminum and $C_{14-20}$ olefins. This bottoms fluid is conveyed via conduit 34 to second ethylene displacement unit 35 maintained under ethylene displacement conditions. Ethylene is fed to second ethylene displacement unit 35 in an amount sufficient to complete the displacement of non-ethyl alkyl groups bonded to aluminums forming a second ethylene-displaced product comprising mainly ethylene, $C_{4-20}+$ α-olefins and TEA.

This second ethylene-displaced product is transferred via conduit 40 to distillation unit 41 which functions to distill ethylene, $C_{4-12}$ α-olefin and part of the remaining TEA overhead. This distillate is combined via conduit 42 with the overhead stream from distillation unit 33 and the combined stream 43 is subjected to flash vaporization in flash unit 45 to remove ethylene. The ethylene-depleted bottoms mixture from flash unit 45 is conveyed via conduit 46 to distillation unit 47 wherein $C_{4-6}$ α-olefins are distilled overhead and the bottoms stream comprising TEA and residual $C_{8-12}$ olefins is conveyed via conduit 48 back to first ethylene chain growth reaction zone as part of the TEA feed. This completes the ethylene displacement loop.

The bottoms from distillation unit 41 are conducted via conduit 50 to a mid-point in vacuum rectification column 51 maintained at 15–30 torr (15 to 30 mm mercury or about 0.3 to 0.6 psia). In column 51, TEA is distilled overhead for recycle and the bottoms stream comprising mainly heavy $C_{14}+$ olefins and heavy aluminum alkyls is conveyed to a disposal area as a purge stream.

The following example illustrates the operation of butene displacement under different pressures and temperatures.

EXAMPLE

The aluminum alkyl feed contained about 88 weight percent of tri-$C_2$ to $_{18}$ alkyl aluminums, peaked at $C_6$, and 12 weight percent of $C_6$ to $C_{20}+$ olefins. The weight percent Al in the total feed was about 7.8. The butene feed was a mixture of about 45 wt % butene-1 and 55 wt % butene-2. The butene feed rate was about 46 grams/min and the aluminum alkyl feed rate was about 12 grams/min at 220° F. The butene feed temperature was adjusted (about 550° to 750° F.) to achieve the desired adiabatic mixing temperature. The feed temperatures were controlled by heaters on the feed tubes to the reactor. A Chemineer Kenics static mixer with internal volume of 0.8 cc was used as the reactor. The 0.8 cc static mixer had 17 elements, i.e., right and left-handed helices. The dimensions were 0.188" OD, 0.132" ID and 4.875" length. Very good mixing was achieved in the static mixer.

Reaction temperatures were varied between 535°–620° F. and pressures between 65–1700 psig. For product analysis, the mass from the reactor was quenched with cold pentane in a cooling tee and separated into gas and liquid product portions which were sampled and analyzed. The % displacement decreased in a straight line with reaction pressure without the expected break due to transition from a liquid to a two-phase, vapor-liquid system. For example, at a reactor temperature of 540° F. the % displacement went smoothly from about 65 (84% equilibrium displacement) at 1700 psig down to about 20% (26% equilibrium displacement) at 65 psig at a residence time of 0.14 second. The ratio of reactor volume to feed rate and, therefore the residence time, can be increased to increase the % displacement to the desired percentage for operation at any selected pressure. Under normal operation the liquid product was clear and aluminum deposition or coking was not observed. The static mixer, therefore, permitted smooth operation regardless of whether the reaction mass constituted single phase liquid or vapor systems, or a two-phase, vapor-liquid system. This invention thus permits butene displacement to be efficiently operated even at moderate pressures without aluminum alkyl decomposition and avoids the need for using very high pressure equipment.

We claim:

1. In a process for making higher α-olefins from ethylene by chain growth comprising the steps of feeding ethylene and an alkyl aluminum compound to a reaction zone maintained under chain growth conditions to produce tri-$C_{2-20}+$ alkyl aluminum compounds, feeding at least a part of said tri-$C_{2-20}+$ alkyl aluminum compounds and butene as reactants to a displacement zone maintained under displacement conditions to form a butene displacement product comprising mainly tributyl aluminum, ethylene and $C_{4-20}+$ α-olefins, removing ethylene and $C_{4-10}$ α-olefins from said butene displaced product, conveying the remainder of said butene displaced product to a second ethylene chain growth reaction zone maintained under chain growth conditions and feeding ethylene to said second ethylene chain growth reaction zone thereby forming a second chain growth product, the improvement comprising employing in said displacement zone a flow through reactor and providing radial mixing of said tri-$C_{2-20}+$ alkyl aluminum compounds and said butene in said reactor.

2. The process of claim 1 wherein said displacement is carried out at a temperature of about 500° to 750° F. and a pressure of about 50 to 2000 psig.

3. The process of claim 1 wherein the reactants in said displacement zone form a two-phase, vapor-liquid system.

4. The process of claim 1 wherein the reactants in said displacement zone form a vapor-phase system.

5. The process of claim 3 wherein from about 2.5 to 50 moles of butene per mole of alkyl aluminum is fed to said displacement zone and the residence time in said reactor is from about 0.1 to 2 seconds.

6. The process of claim 1 wherein the butene comprises at least about 20 weight percent 1-butene and up to about 80 weight percent 2-butene.

7. The process of claim 6 wherein the butene comprises about 45 weight percent 1-butene and about 55 weight percent 2-butene.

8. The process of claim 1 wherein said reactor contains means for repeatedly forcing the material at the center of the reactant stream to the outer wall of the reactor wall and back again so as to accomplish said radial mixing.

9. The process of claim 8 wherein said means is a static mixer comprising a series of alternating right and left-hand helices so as to impart both flow division and radial mixing of the reactants.

10. The process of claim 1 wherein said radial mixing is provided in the first 1/10 to ½ of the length of said reactor.

11. The process of claim 1 wherein said reactor contains a static mixer, said displacement is carried out at a temperature of about 500° to 750° F. and a pressure of about 50 to 2000 psig, said butene contains 20 to 100 weight percent 1-butene and 0 to 80 weight percent 2-butene, from about 2.5 to 50 moles of butene per mole of alkyl aluminum compound is fed to said displacement zone, and the residence time in said reactor is from about 0.1 to 2 seconds.

12. The process of claim 10 wherein the reactants in said displacement zone form a two-phase, vapor-liquid system.

13. The process of claim 10 wherein the reactants in said displacement zone form a vapor-phase system.

14. The process of claim 10 wherein said pressure is from about 150 to 800 psig.

15. The process of claim 11 wherein said static mixer extends for the first 1/10 to ½ of the length of said reactor.

16. The process of claim 1 wherein a portion of said tri-$C_{2-20}+$ alkyl aluminum compounds from said reaction zone and ethylene are fed to an ethylene displacement loop.

* * * * *